Figure 1:
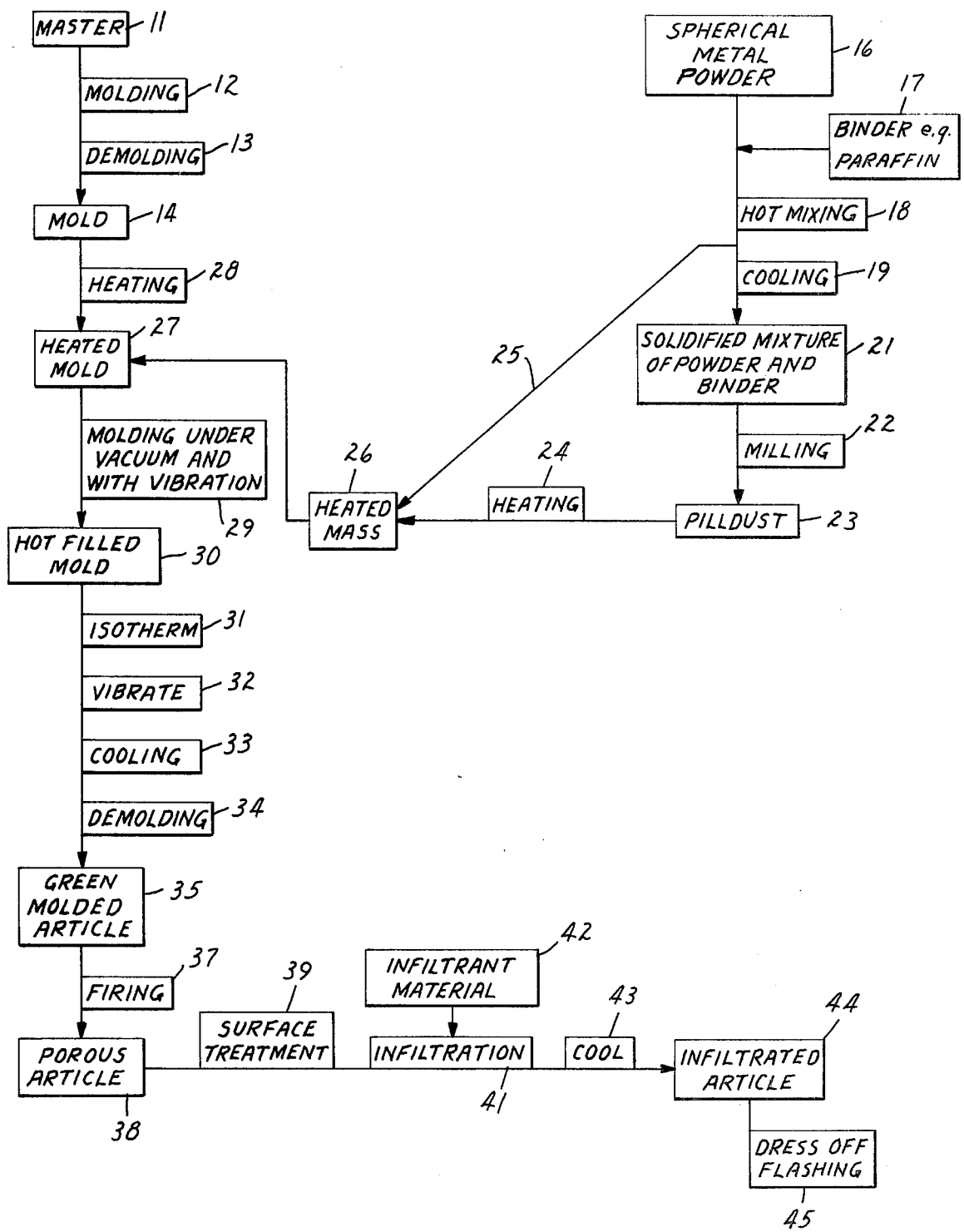

United States Patent [19]

Dillon et al.

[11] 4,431,449
[45] Feb. 14, 1984

[54] INFILTRATED MOLDED ARTICLES OF SPHERICAL NON-REFRACTORY METAL POWDERS

[75] Inventors: Kenneth R. Dillon; Richard L. Terchek, both of St. Paul, Minn.

[73] Assignee: Minnesota Mining and Manufacturing Company, St. Paul, Minn.

[21] Appl. No.: 499,412

[22] Filed: Jun. 1, 1983

Related U.S. Application Data

[63] Continuation of Ser. No. 836,782, Sep. 26, 1977.

[51] Int. Cl.$^3$ .............................................. B22F 3/00
[52] U.S. Cl. ........................................ 75/246; 419/26; 419/27; 419/36; 419/38; 419/48; 428/567
[58] Field of Search .................. 419/26, 27, 36, 38, 419/48; 75/246, 247; 428/567

[56] References Cited

U.S. PATENT DOCUMENTS

| | | | |
|---|---|---|---|
| 2,783,145 | 2/1957 | Boyce | 428/567 |
| 3,307,924 | 5/1967 | Micheal | 428/567 |
| 3,343,954 | 9/1967 | Brab | 428/567 |
| 3,459,547 | 8/1969 | Andreotti et al. | 428/567 |
| 3,729,794 | 5/1973 | Douglass | 75/200 |
| 3,823,002 | 7/1974 | Kirby, Jr. et al. | 428/567 |

Primary Examiner—Brooks H. Hunt
Attorney, Agent, or Firm—Donald M. Sell; James A. Smith; David R. Cleveland

[57] ABSTRACT

A molded, non-refractory metal article is made by molding in a flexible mold a plastic mixture of non-refractory, spherical metal powders and a heat-fugitive binder comprising thermoplastic material to form a green article of predetermined shape and dimensions, heating the green article to remove said binder and consolidate the non-refractory spherical powders in the form of a porous, monolithic skeleton of necked particles of non-refractory metal, infiltrating the skeleton with a molten metal having a melting point that is at least 25° C. less than the melting point of the lowest melting of said spherical, non-refractory metal particles, and cooling the infiltrated skeleton thereby forming a homogeneous, void-free, non-refractory metal article of two intermeshed metal matrices.

29 Claims, 2 Drawing Figures

INFILTRATED MOLDED ARTICLES OF SPHERICAL NON-REFRACTORY METAL POWDERS

This is a continuation of U.S. application Ser. No. 836,782 filed Sept. 26, 1977.

This invention relates to a process for forming infiltrated, molded metal articles made from metal powders and the articles so made. In another aspect, it relates to a process for making infiltrated, molded metal articles by using metal powders and a binder comprising a thermoplastic material. In a further aspect, it relates to a powder metallurgy process for forming molds or dies and to articles so made. In yet a further aspect, it relates to a process for making dental prostheses and to the articles so made.

In the art of powder metallurgy a significant advancement is that disclosed in U.S. Pat. No. 3,823,002, (Kirby et al). Kirby et al disclose the production of molded refractory articles from a plastic mixture of refractory multimodal granules and a fugitive thermoplastic organic binder, which mixture is shaped to form a green article that is heated to remove the binder and form a porous skeleton having no perceptible necking between the largest contiguous granules present in the skeleton, the latter then being infiltrated with a molten infiltrant of a second metal with a melting point less than one-half of the refractory powder.

Briefly, this invention comprises, in one aspect, molding a plastic mass comprising a mixture of spherical, non-refractory metal powder and a heat-fugitive organic binder comprising a thermoplastic material to form a green article replica of a master, heating the molded green article to drive off or remove the binder and lightly sinter the non-refractory particles and form a porous, non-refractory, monolithic skeletal article having necking between contiguous particles thereof, and infiltrating the skeletal article with a melt of metal having a melting point which is at least 25° Kelvin lower than the lowest melting point of the lowest melting said non-refractory spherical metal powder.

The resulting shaped, monolithic, metal article of this invention is a homogeneous infiltrated article comprising as a major portion a first continuous phase of spherical, non-refractory metal particles which are metallurgically integral at their contiguous points of contact in the form of a skeleton of interconnected globules with perceptible necking, when viewed by a light microscope, between the largest contiguous particles thereof, and a second continuous phase of a metal which has a melting point of at least 25° Kelvin lower than the melting point of the lowest melting said spherical non-refractory particles and which occupies the volume of said article not occupied by said skeleton of spherical particles, said article thereby comprising two intermeshed matrices and being substantially void free.

Unless the context indicates otherwise, "homogeneous" as used herein means that when a representative cross-section of either the interior or the peripheral portion of the molded, infiltrated article is examined with a light microscope at a magnification at which the two phases are discernible, e.g. 150X, no significant deviation appears in the number of spherical, non-refractory particles in a given area, and that the infiltrant is uniformly dispersed around and between the non-refractory spherical particles, and that there is no unique axis or densification of the spherical particle in any portion of the article (especially in the peripheral portion, i.e., the portion adjacent the surface of the article), such as that indicative of the use of pressure to introduce coherence to the non-refractory spherical metal particles. These homogeneous articles are essentially free of interior and surface defects and therefore exhibit uniform physical, chemical, electrical and mechanical properties. In addition, the two intermeshed homogeneous matrices impart additional desirable properties, e.g. resistance to wear and to impact.

Some shrinkage occurs in the process of this invention. Exactly how much shrinkage occurs depends upon the process parameters chosen, especially the material used to produce a mold from the master and the temperature at which light sintering is accomplished. Once the magnitude of process shrinkage has been determined for given process parameters, it can be compensated for, e.g. by machining a master to oversize. With compensation for process shrinkage, a precision tolerance, i.e. the percent deviation of the final infiltrated article from blue print specification, of better than about ±0.2% can be obtained, e.g. ±0.1.

The homogeneity and precision tolerance of the non-refractory metal articles of this invention means that these articles are particularly well-suited for applications where close dimensional tolerances are desirable, such as articles with intricate or complex shapes and surfaces with fine details, e.g. dental prostheses and injection molding dies.

Figure 2:
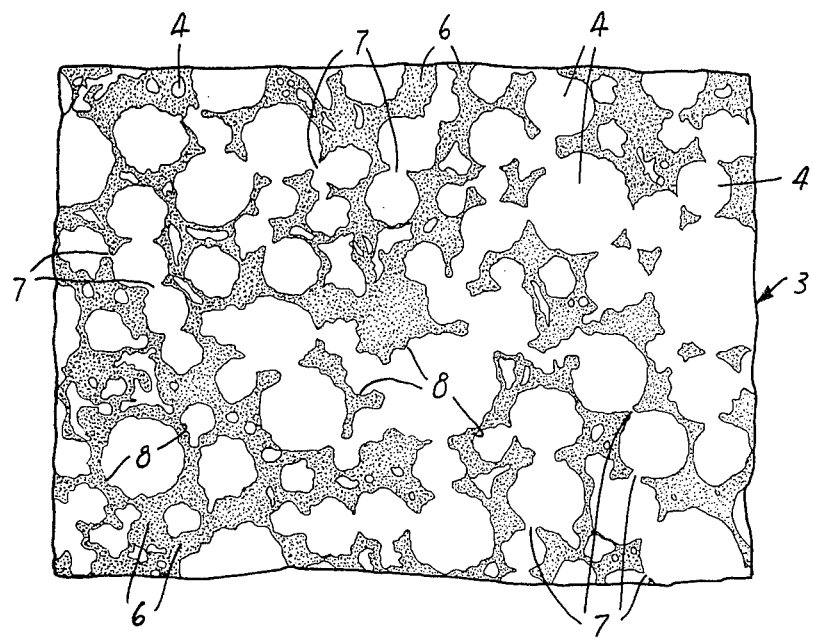

In the accompanying drawing,

FIG. 1 is a flow diagram showing the manufacture of a molded article of this invention; and FIG. 2 is a pen-and-ink sketch of a photomicrograph of an infiltrated non-refractory skeleton of a molded article of this invention.

In the practice of this invention, a metal powder composed of spherical particles of non-refractory metal is used to make a monolithic skeleton or matrix thereof. "Non-refractory" as the term is used herein means metals with melting temperatures in the range of about 1000° C. to 1800° C. (1273° K. to 2073° K.). "Spherical" as used herein means essentially spherical and is inclusive of spheroidal, oblate, or prolate. Minor deviation from precise sphericity does not adversely affect the use of powders in this invention. Representative non-refractory metals useful in this invention include iron, cobalt, and nickel and their alloys. Typical alloying elements for such alloys include chromium, molybdenum, tungsten, carbon, silicon and boron, and combinations thereof. Unless otherwise indicated, it is to be understood that "metal" as used herein includes elemental metal and alloys. The production of spherical metal particles, useful in the practice of this invention, is described in the art, e.g. U.S. Pat. Nos. 3,988,524, 3,258,817 and 3,041,672. Commercially available non-refractory spherical particles or powders which can be used in this invention include alloys number 1, 21, and 157 sold by Cabot Corp. under the "Stellite" trademark, Special Metals Corporations' Co-6 alloy sold under the "Vertx" trademark, and stainless steel type 410 (American Iron and Steel Institute specification). These commercially available powders generally exhibit a mono-modal size distribution curve and comprise a mixture of fractions of small particle sizes and fractions of larger particle sizes. Because of their commercial availability, these mono-modal powders are preferred in the practice of this invention and the properties of the molded articles of this invention can be achieved without requiring he use of multi-modal powders. Mixtures of these commercially available powders can be used in the practice of this invention. The size of the spherical metal powders useful in this invention is a broad distribution of about 1 to 200 μm (micrometers) diameter particles with those less than 44 μm (−325 mesh U.S. Sieve Size) in diameter being preferred for optimum surface finish. Commercially available spherical metal particles may contain a small proportion of particles with a diameter of less than 1 μm; such small particles do not adversely affect this invention as long as the proportion of such particles is not sufficient to prevent contact between the larger particles present and therefore interfere with efficient packing. The calculated surface area of spherical particles falling within the size range preferred in the practice of this invention is about $1.8 \times 10^{-2}$ m$^2$/g to $14.2 \times 10^{-2}$ m$^2$/g.

The desired surface geometrics of the infiltrated molded article will be a principle factor in determining the particle size and size distribution of spherical particles to be used in making such articles. If intricate detail or high surface finish is desired, the particle size distribution chosen will have a larger proportion of small diameter particles; conversely, if little detail or a rough surface finish is required, a distribution with a larger proportion of large diameter spherical particles may be employed.

The use of spherical metal particles produces a number of significant advantages over irregularly shaped metal particles. Irregularly shaped granules, because of the possibility of multiple, interparticle contacts between any two given particles, tend to form interparticle mechanical bridges which adversely affects their flow characteristics. In contrast, any two spherical particles are capable of but a single interparticle contact and therefore do not mechanically bridge. Hence, the irregularly shaped particles neither flow as readily nor do they fill intricate mold details as completely as spherical particles, even when vibrated. Higher loading of the organic binder is possible with spherical particles. "Loading" refers to the mass of particles that may be carried in a given amount of softened organic binder. Spherical particles pack more efficiently than irregularly shaped particles and therefore less binder is required for a given mass of spherical particles. Better packing also produces metal skeletons with a more uniform porosity prior to infiltration. By "porosity" we mean the interstitial passageways between the lightly sintered spherical metal particles of which the skeleton (or first continuous phase) is composed.

The volume of the infiltrated article to be occupied by the skeleton of spherical metal particles will also determine the particle size and size distribution of particles chosen. The infiltrated article will contain as the major portion thereof lightly sintered spherical metal particles, with at least 60 volume percent preferably, and more preferably, at least 65 volume percent) and not in excess of about 80 volume percent spherical metal particles. The volume percent of the article occupied by spherical metal particles is controlled by the degree of loading of the organic binder. Variation of particle size and size distribution to adjust loading is known in the art, e.g. see R. K. McGeary, *J. Am Ceram. Soc.* 44, 513-22 (1961).

Organic binders suitable for use in this invention are those which melt or soften at low temperatures, e.g. less than 180° C., preferably less than 120° C., thereby providing the metal powder-organic binder mixture with good flow properties when warmed and yet allow the powder-binder mixture to be solid at room temperature so that a green article molded therefrom can be normally easily handled without collapse or deformation. The binders used in this invention are those which are heat fugitive, that is, which burn off or volatilize when the green article is heated without causing internal pressures on the resulting non-refractory skeletal article due to its vaporization and without leaving substantial binder residue on the skeletal article resulting from such heating step.

Organic thermoplastics, or mixtures or organic thermoplastics with organic thermosets, are mixed with non-refractory spherical metal powders to form a moldable pastelike or plastic mass when the resulting binder-powder mixture is heated. Examples of thermoplastic binders include paraffin, e.g. "Gulf Wax" (household grade refined paraffin), a combination of paraffin with a low molecular weight polyethylene, mixtures containing oleic or stearic acids or lower alkyl esters thereof, e.g. "Emerest" 2642 (polyethylene glycol distearate, average molecular weight of 400) as well as other waxy and paraffinic substances having the softening and flow characteristics of paraffin.

Representative thermosetting materials which can be used in combination with thermoplastics as binders include epoxide resins, e.g. diglycidyl ethers of bisphenol A such as 2,2-bis[p-(2,3-epoxypropoxy)phenyl]-propane, which can be used with appropriate curing catalysts. Care must be exercised so as not to thermally induce cross-linking during the mixing and molding steps when thermoplastic-thermoset mixtures are used as binders. Once the softened thermoplastic-thermoset binder mixture and the spherical metal particles have been placed in the warmed mold and vibrated, curing may be initiated by further warming the mold. Thermoplastic-thermoset binder mixtures tend to produce green articles that have stronger green strength and thus are more handleable than green articles made with just a thermoplastic as the binder.

The spherical metal powder and organic binder are preferably mixed in a warmed blending device, e.g., a sigma blade mixer, the temperature being sufficiently high to soften the organic binder thereby allowing the powder and binder to be homogeneously mixed. The particular amount of binder used depends upon the particle size and size distribution of spherical metal particles employed. Sufficient binder should be used, e.g. 2 to 10 parts by weight if 100 parts metal power is employed, such as will permit the spherical particles to flow into and optimally occupy the mold, thereby eliminating bulk and surface density variations in the molded article. The power-binder mixture can be warmed to form a plastic mass and directly transferred into a flexible mold. Alternatively, the warm metal powder-organic binder mixture can be cooled and the resulting solid milled into a granular, free-flowing state, (such a granular material being referred to as "pill dust"), and later warmed and poured into the mold.

In order to provide a mold for molding the pill dust or warm plastic mass into a desired shape, a pattern or replica is made from a master. A molding material is poured around the master in a suitable container, the molding material cured, and the master withdrawn to form a mold which is capable of reproducing substantially identical copies of the master, including fine details and cross sections, in accordance with this invention.

The metal articles produced in the practice of this invention can have a working surface (that is, the working portion) that comes into contact with and effectuates a deformation in a material to be worked, and a support portion that maintains the working surface in the proper position to produce the desired deformation. For example, a core pin, produced according to this invention, can be used to form a hole in an injection molded plastic part. The working surface of such a core pin is that portion that actually comes into contact with the plastic material to be molded and the support portion holds the core pin in position so that the desired hole is produced.

The preferred master has the working surface and support portion mounted on and extending out of or away from a base. The base may be the remainder of the material from which the working surface-support portion was produced, or the working surface-support portion may be mounted on a separate base after production. A mold of the master is produced by placing the master in a suitable container, pouring the molding material around the master and curing the molding material. If the preferred master is used, in the later light sintering step, a one-piece porous metal skeleton with a working surface-support portion mounted on a base will be produced. This is desirable because the metal skeleton so produced may be infiltrated by passing the infiltrant metal through the base prior to entering the body of the porous metal skeleton beneath the support portion-working surface. Infiltrating the metal skeleton through the base permits the infiltrant to solubilize, i.e. to become enriched with the metal of which the working surface-support portion is composed, prior to infiltrating the body of the skeleton beneath the working surface-support portion. Such enrichment of the infiltrant metal reduces dimensional changes that would occur if the body of the skeleton were to be infiltrated with unenriched infiltrant metal and the skeleton metal were to be significantly solubilized in this unenriched infiltrant. After infiltration in this manner, the base may be completely removed or machined to a desired configuration to be used as the support portion for the working surface. In this latter instance the base functions as both the support portion and base and therefore the working surface may be mounted directly on the base.

The molding materials which can be used in the practice of this invention are those which cure to an elastic or flexible rubbery form and generally have a Shore A durometer value of about 25-60, and reproduce the fine details of the master part without significant dimensional change, e.g. without more than 1 percent linear change from the master. The molding materials should not be degraded when heated to molding temperatures, e.g. 180° C., and should have a low cure temperature, e.g. room temperature. A low temperature curing molding material will form a mold which maintains close dimensional control from master to mold. A high temperature curing molding material will generally produce a mold having dimensions substantially different from those of the master. To maintain dimensional control, it is preferable that the mold material have a low sensitivity to moisture. Examples of suitable molding materials are curable silicone rubbers, such as those described in Bulletin "RTV" 08-347 of January, 1969, of the Dow Corning Co., and low exotherm urethane resins. Such molding materials cure to an elastic or rubbery form having a low post cure shrinkage.

The amount of molding material used to form a mold of the master can vary depending on the particular molding material used and the shape of the master. It has been found that about 10–14 cubic centimeters of molding material for each cubic centimeter of the master will form a mold which retains the desired flexible properties and also has sufficient strength to support the small hydrostatic head produced by the plastic powder-binder mass in the mold before solidification of the binder.

The molding conditions, hereinafter discussed, for molding the articles of this invention permit the use of an inexpensive soft, elastic or rubbery mold because the only pressure applied is the hydrostatic head of the plastic powder-binder mixture in the mold, which pressure is very small and causes negligible distortion. The mild molding conditions thus help ensure a precisely molded green article even though a highly deformable mold is used. In addition, the molding technique results in a molded green article with a uniform density because of the advantageous flow characteristics of the spherical powder.

The powder-binder mixture or pill dust, warmed 10° C. to 20° C. or more above the softening point of the binder component, can be fed into the vibrating elastic mold that has been preheated to approximately the same temperature as the powder-binder mixture, and the mold and its contents can then be evacuated. By choosing the proper size distribution of spherical non-refractory particles and a suitable organic binder, the consistency of the powder-binder mixture is such that when heated above the melting point of said binder in a vacuum, the mixture can be molded with only slight vibration to ensure removal of air pockets or gas bubbles.

After filling the warmed, evacuated mold, vibration of the mold is discontinued and the mold is isothermed, e.g. maintained at a constant temperature 10° C. to 30° C. above the softening point of the binder, for a sufficient period, e.g. about 1 to 24 hours, to ensure uniform complete filling of the mold. The mold and its contents are vibrated for a short period prior to cooling.

Cooling the mold and its contents to room temperature solidifies the organic binder and forms the green molded article. If the binder melts at a fairly low temperature, e.g. 35° C.–40° C., then it is necessary to cool, e.g. to 0° C. to 5° C., the mold and its contents to the point where the binder becomes fairly rigid, preferably in a desiccator to reduce moisture condensation. The solid green article can be easily demolded by application of a vacuum to the exterior of the flexible mold. Vacuum demolding allows easy demolding of shapes that have undercuts. The resulting, demolded, green article is a faithful replica of the master. This molded article has good green strength due to the hardened matrix of organic binder supporting the non-refractory spherical metal particles. The non-refractory powder is homogeneously dispersed in the organic binder matrix, conducive to forming a green article with uniform density (because of the uniform distribution of powder within the binder) and to forming a skeleton therefrom with corresponding uniform porosity when the binder is removed.

The uniform density of the green molded article is important in the subsequent firing and infiltration steps. A uniform green density will minimize or prevent shape distortions when the green molded article is heated and infiltrated. Also, a uniform density will minimize or prevent the formation of localized pockets of infiltrant material which otherwise would make the ultimate finished non-refractory article exhibit unstable and non-uniform electrical or physical properties.

To form the skeletal matrix, the green molded article is preferably packed in a gently vibrating bed of non-reactive refractory powder, e.g. alumina or silica, to prevent sagging and loss of dimension upon heating in a programmable furnace to a temperature of about 900° C. to 1400° C. Heating the molded green article removes the organic binder and lightly sinters or tacks the non-refractory particles to form a metallurgically integral, handleable, porous, non-refractory, monolithic article, or skeleton. The term "metallurgically integral" as used herein means that there is solid state interatomic diffusion, i.e. there is a solid state bond formed, between contiguous spherical metal particles. This heating step, in addition to removing the binder, causes first stage of sintering of the spherical particles, i.e. formation of interparticle necks, thereby producing a monolithic artice. Programmed heating is preferably employed so as to cause only minimal spherical particle sintering or tacking at their contiguous points of contact. Programmed heating avoids the significant shrinkage that would occur if heating and sintering were continued beyond the first stage, thereby producing undesirable skeleton shrinkage and increase in density as interstitital pore volume decreased and the particles become joined by larger necks. Programmed heating also avoids the introduction of internal and external cracks otherwise produced by rapid evolution of gaseous binder if the green molded article were to be rapidly heated to the light sintering temperature. Small green molded articles are generally capable of being heated at a more rapid rate than larger articles. A heating schedule found suitable for articles as large as 5 cm cubes when, for example, polyethylene glycol distearate is used for the organic binder, is as follows:

Step 1 from room temperature to 200° C. (about 43° C. per hour)

Step 2 from 250° C. to 400° C. (about 7.5° C. per hour)

Step 3 from 400° C. to the light sintering temperature (about 100° C. per hour).

This programmed heating is carried out under a protective atmosphere, e.g. hydrogen-argon, nitrogen, hydrogen-nitrogen, hydrogen, dissociated ammonia, and other neutral or reducing atmospheres known in the powder metallurgy art to prevent oxidation of the metal particles.

Heating the green molded articles to a temperature in excess of about 1020° C. when alumina is used as the refractory non-reactive support material may cause some alumina to adhere to the green molded article. For this reason, when a final light sinter temperature in excess of 1020° C. is intended, the light sintering process may be stopped at 1020° C., and the resulting coherent, handleable molded article may be cooled and removed from the alumina bed. Alumina adhering to the surface of the article is gently removed and the article heated to the desired final light sintering temperature without the necessity of support in non-reactive refractory powder. Where light sintering temperatures of less than 1020° C. are employed, surface adhering support material can be removed by gentle brushing with a camel's hair brush.

To ensure complete filling of the interstitial pore volume, if a mass of infiltrant metal in excess of the calculated interstitial pore volume is used, excessive wetting of the skeleton and accumulation or buildup of the infiltrant on the exterior surface of the article, or "blooming" often will result. If excessive skeleton wetting is minimized by using slightly less infiltrant than necessary to completely fill the voids of the metal skeleton, this will leave uninfiltrated voids in the final composite and thereby reduce its mechanical strength and uniformity of electrical and physical properties.

Surface blooming can be reduced or prevented in this invention by coating the exterior surface of the lightly sintered metal skeleton with a thin layer of zirconia powder, e.g. by lightly spraying the exterior of the metal skeleton with a suspension of zirconia powder in a readily evaporated or volatilized carrier, e.g. acetone. The zirconia powder coating reduces surface buildup of the infiltrant and permits the use of a mass of infiltrant metal in excess of that necessary to just fill the interstices of the metal skeleton without the occurrence of blooming (or uninfiltrated voids). Contact between those exterior areas of the skeleton where infiltration is to occur, e.g. the base, and the zirconia powder is to be carefully avoided, e.g. by covering such areas with masking tape. The zirconia coating step may be used selectively or eliminated if some amount of surface blooming is desired, e.g. to produce a molded article that appears as though it was formulated completly from the infiltrant metal, e.g. a decorative art object with a cobalt alloy metal skeleton infiltrated with silver or a silver alloy.

The porous metal skeleton (preferably zirconia-treated as described above) is infiltrated or infused with a metal or alloy that melts at a temperature below the melting point of the spherical metal particles of which the metal skeleton is composed and preferably has the properties discussed below. Surprisingly, infiltration can be accomplished without substantial dimensional change by using as the infiltrant a metal which melts at a temperature that is as little as 25° K. less than the melting point of the lowest melting skeleton particles. When the infiltrant melting point, $MP_i$, and the melting point of the metal of which the spherical particles is composed, $MP_{sp}$, are both expressed in degrees Kelvin, workable $MP_i/MP_{sp}$ ratios of as high as 0.98, with 0.95 or less being preferred, can be used. As this ratio decreases, dimensional changes also decrease, which means the lower limit of the infiltrant metal melting point-skeleton metal melting point ratio is determined by the desired properties of the final infiltrated articles.

Infiltrants with the preferred properties discussed below generally have melting points greater than about 700° Kelvin and therefore the lower limit of the melting point ratio is about 0.5 with 0.6 being preferred.

Infiltration of the metal skeleton occurs uniformly by capillary action without pressure applied to the infiltrant and without the formation of localized pools of infiltrant material in the non-refractory skeleton. The non-refractory metal skeleton can be supported on a bed of refractory, non-reactive powder. The bed is arranged so that the solid infiltrant material, which may be in the form of powder, shot or bars, is not in direct contact with the metallic skeleton. As the infiltrant melts, it flows under the influence of gravity toward that area of the metal skeleton through which infiltration is to occur, e.g. the base, contacts the skeleton while liquid, and enters the skeleton by capillary action. Direct contact between the solid infiltrant material and the metallic skeleton can cause bonding of the two during heating. In addition, differences in the thermal coefficients of expansion or sintering rate between the infiltrant and the skeleton will cause stress and possible cracking of the base of the skeleton. No contact between the solid infiltrant and the metal skeleton is therefore preferred. Because the infiltrant is uniformly distributed throughout the non-refractory skeleton body, uniform strength and acceptable electrical characteristics are obtained, with minimal shape distortion of the final infiltrated object due to the thermal-expansion coefficient differences discussed above.

The metal infiltrant used will be chosen to suit the end use for the finished part. When an electrical discharge machining electrode is desired, infiltrants having good electrical conductivity, e.g. copper, silver and alloys of these metals, can be used. Where a harder or stronger finished article is desired, e.g. as for structural parts, molds or dies, the infiltrant material as well as the spherical metal particles can be composed of hardenable alloys which can be further treated to increase the hardness and strength of the article. Still other metals and alloys having a melting point below that of the non-refractory skeleton can be used as infiltrants.

The choice of infiltrant metal is preferably those metals in which the skeleton metal is substantially insoluble. Gross dimensional changes and distortion would occur if the infiltrant substantially dissolved the skeleton metal. Major solubilization of the skeleton metal in the infiltrant can be minimized by using an infiltrant metal that has been saturated with the metal out of which the skeleton particles were manufactured. As discussed above, solubilization can also be minimized by infiltrating the metal skeleton through a base. Additionally, the molten infiltrant metal should wet the non-refractory skeleton metal in order to achieve capillary infiltration. Excess infiltrant metal, e.g. up to a volume about 25% greater than the calculated total interstitial pore volume, can be used if the exterior of the metal skeleton has been coated with zirconia powder prior to infiltration.

The length of time at infiltration temperature and the infiltration temperature used will be a function of the size, the wetting characteristics, and the interstitial pore size of the non-refractory metal skeleton. At a temperature slightly above the melting point of the infiltrant, thirty minutes is sufficient to infiltrate a cube shaped skeleton with a volume as large as 130 cc.

After infiltration, the article is cooled and the exterior zirconia coating is removed, e.g., by peening with a glass bead peening apparatus (Empire Abrasive Equipment Corp. Model No. S-20) at a pressure of 1.4 to 2.8 kg/cm$^2$ using an 8 mm diameter orifice. If an age hardenable infiltrant is employed, e.g. copper alloyed with nickel (15%) and tin (7%), or if the metal skeleton is hardenable with infiltrated article may be subjected to a low temperature aging cycle to increase hardness and/or wear resistance. Lastly, excess infiltrant or the superfluous base is machined or cut away from the shaped composite or working surface producing the finished infiltrated molded metal article.

A tabulation of representative systems of spherical metal particles and infiltrants is shown in Table I. The melting points in degrees Kelvin and the ratio of the melting points is tabulated.

Table II contains the elemental compositions of the metals in Table I.

TABLE I

| Spherical Metal Particles | | Infiltrant | | $MP_i/MP_{sp}$ |
|---|---|---|---|---|
| Type | MP, °K. | Type | MP, °K. | ratio* |
| "Vertx" Co-6 | 1533 | copper | 1356 | 0.88 |
| "Vertx" Co-6 | 1533 | phosphor bronze | 1333 | 0.87 |
| "Vertx" Co-6 | 1533 | beryllium-copper | 1144 | 0.75 |
| "Stellite" 1 | 1503 | silver - 72% copper - 28% | 1052 | 0.70 |
| "Stellite" 1 "Vertx" Co-6 (equal parts) | 1503 | copper | 1356 | 0.90 |
| "Stellite" 1 | 1503 | silver | 1233 | 0.82 |
| "Stellite" 157 | 1403 | Ni - 5% Fe - 5% Mn - 5% Cu - bal | 1333 | 0.95 |
| "Stellite" 21 | 1553 | gold - 78% platinum - 22% | 1201 | 0.77 |
| Stainless Steel A.I.S.I. 410 | 1755 | copper | 1356 | 0.77 |
| "Stellite" 92 | 1403 | copper - 70% tin - 30% | 1033 | 0.74 |
| Iron | 1807 | copper - 70% tin - 30% | 1033 | 0.57 |

*$MP_i/MP_{sp}$ is the ratio of the melting point of the infiltrant metal to minimum melting point of the spherical particles.

TABLE II

| Type of Spherical Metal Particles | Composition, wt % | | | | | | | | | | | |
|---|---|---|---|---|---|---|---|---|---|---|---|---|
| | Cr | C | Si | Mo | Ni | Fe | Co | W | B | Cu | P | Be | Others |
| "Vertx" Co-6 | 29 | 1.1 | 0.94 | 0.12 | 2.9 | 0.81 | Bal. | 4.05 | | | | | |
| "Stellite" 1 | 30 | 2.5 | 1.0 | | 3.0 | 3.0 | Bal. | 1.2 | | | | | 1.0 |
| "Stellite" 157 | 21 | 0.07 | 1.6 | | | | Bal. | 4.5 | 2.4 | | | | |
| "Stellite" 21 | 27 | .25 | | 5.5 | 2.8 | 2.0 | Bal. | 7.5 | | | | | 2.0 |
| Stainless Steel A.I.S.I. 410 | 12.32 | 0.020 | 0.33 | | .18 | Bal. | | | | | | | |
| "Stellite" 92 | 1.5 | 3.75 | | 10. | | Bal. | | | | | | | |
| Phosphor-bronze | | | | | 1.1 | | | | | Bal. | 0.3 | | |
| Beryllium-copper | | | | | | | 0.2 | | | Bal. | | 1.9 | |

An optical examination of the working surface of the finished article at a magnification of 150X reveals a continuous matrix of essentially spherical particles or interconnected globules in contact with and surrounded by a continuous phase of infiltrant. No evidence of surface cold work, e.g. disturbed surface metal as produced in conventional machining operations, is seen.

FIG. 2 is a view of a metallurgically polished interior cross section of an infiltrated article of this invention of a magnification of 600X. A continuous matrix 3 of essentially spherical metal particles 4 with a distribution of sizes is clearly evident. The continuous phase of metal infiltrant 6 in contact with and intermshed with the skeleton of spherical metal particles or globules is seen with neck formation 7 between particles. At this magnification, deviation 8 from sphericity become apparent. These deviations are the result of partial dissolution of the skeleton metal in the molten infiltrant and are characteristic of the infiltrated metal articles of this invention. Such dissolution causes the slight loss of sphericity and imparts the somewhat globular, erroded appearance to the spherical, interconnected non-refractory spherical metal particles.

The process of this invention described above is illustrated in FIG. 1. A master 11 machined to compensate for inherent shrinkage is molded 12 using a flexible molding material such as "RTV" silicone rubber. The molding material is cured by the appropriate process depending upon the flexible molding compound used, and the machined master is demolded 13 from the cured, solid rubbery mold 14. Non-refractory spherical metal powder 16, e.g. "Vertx" Co-6 cobalt-based powder, of the appropriate size distribution is mixed with a thermoplastic binder 17, e.g. paraffin or a mixture of a thermoplastic and a thermosetting binder, and heated 18. The resulting mass optionally may be allowed to cool 19 to a solid 21, and milled 22 into pill dust, 23, which requires heating 24 before feeding the powder-binder mass 26 to the heated mold 27 or the heated powder-binder or mass 26 can be passed 25 from step 18 directly to the mold 27. The mold 14 is appropriately heated 28 prior to filling with the heated mass 26. The mold and its contents are evacuated while being vibrated 29 to remove air bubbles and completely pack the mold 30. The completely filled mold is isothermed 31 and vibrated 32 briefly prior to cooling 33. Vacuum demolding 34 produces a rigid handleable green molded article 35.

The resulting green molded article 35 is packed in a non-reactive refractory powder and programmably fired 37 to drive off the thermoplastic binder and cause the metal particles to lightly sinter to form a porous metal article 38. The porous article is surface treated 39 and placed in a container suitable for infiltration 41 with, for example, copper 42. After cooling 43, the resulting infiltrated article 44 may be dressed at the site of infiltration to remove irregularities 45. After vacuum demolding the green molded article 35, the flexible mold may be recycled 14 to produce another article.

The infiltrated non-refractory metal articles of this invention are uniformly dense, tough, impact resistant and essentially free of internal and surface defects. They exhibit uniform physical mechanical and electrical properties and a precision tolerance of better than ±0.2% can be achieved. These articles are particularly useful for applications where tough non-refractory articles with close dimensional tolerances are required, such as articles having intricate or complex shapes and surfaces with fine detail, e.g. dental prostheses, dies for metal die casting, and dies for plastic injection molding.

Objects and advantages of this invention are illustrated in the following examples which should not be construed to limit the scope of this invention. All parts are by weight unless otherwise specified.

EXAMPLE 1

One hundred parts of a less than 149 μm (−100 mesh U.S. Sieve) spherical metal powder cobalt-based alloy ("Vertx" Co-6 sold by Special metals Corp.) was mixed with 3.5 parts of polyethylene glycol distearate ("Emerest" 2642, m.p. 36° C.) and the resulting metal powder-binder mixture was warmed to 66° C. The resulting plastic mass are transferred to a cubical cavity (5.08 cm) of a flexible mold made of cured "RTV" silicone rubber which was heated to 66° C. The mold was evacuated to 3 Torr and maintained at 66° C. for 10 minutes, while being vibrated by a Model J 50A Jogger vibrating at a rheostat setting of 80 to 90. The mold and its contents were then repressurized and transferred to an oven to be isothermed at 38° C. for 24 hours. After this isothermal treatment, the mold was again vibrated (with a rheostat setting of 40) for 5 minutes and allowed to cool to room temperature over a 2 hour period. The cooled mold and its contents were placed in a desiccator containing anhydrous calcium sulfate and cooled to about 4° C. for 1 hour. The cooled mold and its contents were removed from the desiccator and the green article was immediately demolded using vacuum demolding. The resulting green article was placed in a graphite boat containing alumina powder ("Alcoa" grade A-100) and vibrated slightly to lightly pack the non-reactive refractory powder around the green article. The boat and its contents were placed in a retort in an electric, cam-controlled Lindberg furnace, and the retort was slowly evacuated to prevent the alumina powder from scattering within the furnace. A vacuum of about 0.5 Torr was sufficient to remove most of the reactive gases and the furnace was rapidly backfilled with an atmosphere of argon containing 5% hydrogen. A dynamic gas atmosphere was maintained during the heating cycle at a flow rate of 85 liters/hour. The furnace was heated from room temperature to 250° C. at a rate of 43° C. per hour, from 250° C. to 350° C. at a rate of 7.5° C. per hour, from 350° C. to 1000° C. at a rate of 100° C. per hour, and maintained at 1000° C. for ½ hour to degrade and remove the binder and lightly sinter the spherical metal particles. Heating was discontinued and the boat and its contents were allowed to cool to room temperature under the dynamic gas atmosphere in the furnace. The lightly sintered skeletal article was removed from the alumina bed and gently brushed with a camel hair brush to remove any surface adhering alumina. The surface of the article was then sprayed with an aerosol suspension made up of 10 g. of zirconia powder (about 1 to 5 μm diameter) in 100 ml acetone. The skeletal article was a cube, and about 0.5 cm of the portion of the 4 faces, adjacent one face or base, was covered with masking tape while the exposed remainder of the five faces was sprayed with the aerosol suspension. The face or base was not covered with masking tape because it was directed away from the zirconia spray and therefore protection of this face was unnecessary. After removal of the masking tape, the green skeletal article was placed at the base of a sloped alumina bed located in a graphite boat. An amount of copper powder ("Gould" type R-64, −100 mesh) was placed on the alumina bed so that upon melting, the liquid copper would flow by gravity downward toward that portion of the skeletal article not covered with zirconia powder, contact the metal skeleton, and infiltrate through the unsprayed exterior surface. The boat and its contents were placed in a molybdenum wound electric furnace, and the furnace was evacuated to 0.05 Torr and back-filled with hydrogen. A dynamic hydrogen atmosphere was maintained at a flow rate of 141 liters/hour while the temperature was raised from room temperature to 1100° C. over a 2 hour period and maintained at that temperature for ½ hour. After infiltration, the resulting infiltrated article was cooled and the exterior zirconia coating was removed by peening it with less than 44 μm glass beads (−325 mesh) through a 8 mm orifice at 1.4 to 2.8 kg/cm² pressure. The peened article was sectioned, metallographically polished, and, when examined at 50X and 750X, the article appeared homogeneous with necking between contiguous sintered spherical particles and no internal cracks, gross porosity or other discontinuities were observed. FIG. 2 is a representation of the appearance of the articles.

EXAMPLES 2-17

A number of runs (Examples 2-17) were carried out by the procedure as described in Example I to make other infiltrated articles of this invention, these further runs being summarized in Table III. In each of these further runs, 100 parts of spherical metal powder were utilized in making infiltrated articles in the form of impact test bars 5.08 cc in size. Where light sinter temperatures in excess of 1020° C. were used, the green molded article was programably heated to about 1020° C., cooled, removed from the non-reactive refractory support and then reheated to the light sinter temperature indicated. Sectioned plate infiltrants were commercially obtained metals while sectioned slab infiltrants were laboratory prepared metals. The results of metallurgical Rockwell "C" and Rockwell "B" hardness tests are given in Table III, as well as Charpy impact tests on notched and unnotched specimens. Rockwell "B" and "C" hardness tests were conducted according to ASTM Specification E18-74. Impact tests were conducted according to ASTM Specification E23-72. Simple beam, Type A, Charpy impact specimens were used but were modified so that cross-section dimensions of 0.399±0.003 in (1.01 cm±0.008 cm) were used. Specimens showing unnotched impact strength were not notched.

In Table III, no internal flaws were exhibited on fracture faces nor on metallographically polished sections of the 131 cc cubes in Examples 9 and 10. This is due in part to the uniform density of the finished infiltrated articles.

TABLE III

| | Spherical Metal | | Binder | | Light sinter temp, °C. | Infiltrant | | Temp of infiltration °C. | Properties of test bar | | | Foot-note |
| | | Particle size | | | | | | | Rockwell "C" hardness | Charpy impact kg-m | | |
| Ex | Type | <μm | Type | Parts | | Type | Form | | | notched | unnotched | |
|---|---|---|---|---|---|---|---|---|---|---|---|---|
| 2 | "Vertx" Co-6 | 149 | "Emerest" 2642 | 3.5 | 1200 | Cu | Powder | 1120 | 24 | 0.34 | 2.07 | 1 |
| 3 | "Vertx" Co-6 | 149 | "Emerest" 2642 | 3.5 | 1240 | Cu | Powder | 1120 | 26 | 0.62 | 2.21 | 2 |
| 4 | "Vertx" Co-6 | 44 | "Emerest" 2642 | 4.67 | 1250 | Cu | Powder | 1125 | 31 | — | 5.5 | |
| 5 | "Vertx" Co-6 | 44 | "Emerest" 2642 | 4.67 | 1100 | Ni - 1.1% P - 0.3% Cu - bal | Sectioned plate | 1100 | 24 | — | — | |
| 6 | "Vertx" Co-6 | 44 | "Emerest" 2642 | 4.67 | 1100 | Be - 1.9% Co - 0.2% Cu - bal | Sectioned plate | 1100 | 25 | — | — | |
| 7 | "Vertx" Co-6 | 44 | "Emerest" 2642 | 4.67 | 1130 | Ni - 15% Sn - 7% Cu - bal | Sectioned slab | 1100 | 30 | 0.28 | — | |
| 8 | "Vertx" Co-6 | 44 | "Emerest" 2642 | 4.67 | 1160 | Sn - 10% Ni - 10% Cu - bal | Sectioned slab | 1079 | 31 | — | — | |
| 9 | "Vertx" Co-6 | 44 | Paraffin | 4.67 | | Cu | Powder | 1100 | — | — | — | 3 |
| 10 | "Vertx" | 44 | "Epon" 828 plus Catalyst; Butyl Stearate; | 1.0 4.0 | 1100 | Cu | Powder | 1110 | — | — | — | 3 |
| 11 | "Stellite" 1 | 44 | "Emerest" 2642 | 4.61 | 1130 | Cu - 28% Ag - 72% | Sectioned Slab | 988 | 29 | — | — | 4 |
| 12 | "Stellite" 1 | 44 | "Emerest" 2642 | 4.61 | 1000 | Ag | Bar | 1125 | 33 | 0.10 | — | 5 |
| 13 | Mixture of equal parts of | | "Emerest" 2642 | 4.67 | 1140 | Cu | Powder | 1100 | 32 | — | 2.8 | |
| | "Stellite" 1 and | 44 | | | | | | | | | | |
| | "Vertx" Co-6 | 44 | | | | | | | | | | |
| 14 | Stainless steel, A.I.S.I. Type 410 | 44 | "Emerest" 2642 | 5.35 | 1020 | Cu | Powder | 1100 | 24 | — | 1.1 | |
| 15 | "Stellite" 157 | 44 | "Emerest" 2642 | 4.67 | 1100 | Ni - 5% Fe - 5% Mn - 5% Cu - bal | Sectioned Slab | 1100 | 29 | — | — | |
| 16 | "Stellite" 1 | 44 | "Emerest" 2642 | 4.61 | 1140 | Ni - 15% Sn - 7% Cu - bal | Sectioned Slab | 115 | 40 | — | 1.38 | |
| 17 | "Stellite" | 44 | "Emerest" | 3.37 | 1000 | Sn - 30% | Sectioned | 900 | 48 | — | 0.21 | 6 |

TABLE III-continued

| | Spherical Metal | | Binder | | Light sinter temp. °C | Infiltrant | | Temp of infiltra- tion °C | Properties of test bar | | | Foot- note |
| | | Particle size | | | | | | | Rockwell "C" hard- ness | Charpy impact kg-m | | |
| Ex | Type | <μm | Type | Parts | | Type | Form | | | notched | unnotched | |
| 92 | | | 2642 | | | Cu - bal | Slab | | | | | |

Footnotes:
. Shrinkage of 0.54% between green molded article and infiltrated compact.
! Shrinkage of 1.98% between green molded article and infiltrated compact.
! A 131 cc cube was produced in this example.
! Shrinkage of 0.25% between lightly sintered metal skeleton and infiltrated compact.
! Shrinkage of 0.32% between lightly sintered metal skeleton and infiltrated compact.
) Shrinkage of 0.40% between green molded article and infiltrated compact.

EXAMPLE 18

Using the procedure of Example 1, a core pin, suitable for plastic extrusion, was prepared. The core pin was approximately ⅛ inches (0.32 cm) in diameter and was used to produce and end-to-end cylindrical hole running along the axis of a cylindrical plastic part about ⅛ inch (0.27 cm) long with an exterior diameter of 0.32 inches (0.813 cm). A "Stellite" No. 1 alloy spherical metal powder (less than 44 μm) was mixed with 4.61 parts of "Emerest" 2642 thermoplastic organic binder. Light sintering of the green molded core pin was continued at 1122° C. for 45 minutes. Infiltration with a copper alloy containing nickel (15%) and tin (7%) was conducted for 45 minutes at a temperature of 1120° C.

The infiltrated pin was machined to permit force fitting into the movable portion of a two-part injection mold. Mating of the core pin on the stationary portion of the injection mold was assured by sanding the pin tip. After installation of the core pin in the movable mold portion, the entire mold was installed in a VanDorn 75 ton (58,000 kg), screw-type injection molding machine with an injection capacity of 5½ ounces (156 g) of polymeric material with the density of polystyrene. One-hundred twenty injection molded plastic parts were produced from polystyrene. Each plastic part was removed from the core pin and ejected from the mold as the movable portion of the mold was opened. A barrel temperature of 193° C. was used along with a maximum injection force of 20,000 psi ($14.1 \times 10^6$ kg/m$^2$). The plastic parts exhibited no extraneous plastic material, indicating that complete closure of the hole had been obtained with the mounted core pin flush against the stationary mold portion. No peening, cracking or wear occurred on the core pin demonstrating homogeneous physical characteristics of the pin.

EXAMPLE 19

A "Stellite" 21 —270 mesh (less than 53 μm) spherical metal powder was used to prepare a gage block using the procedure of Example 1. After light sintering at 1,000° C., the skeleton was sprayed with zirconia powder dispersed in acetone. The coated block was then placed in contact with B dental inlay casting gold of composition, gold (76%), silver (14.3%), copper (7.5%), palladium (2%), and indium (bal). Heating to 1,000° C. for ½ hour in a hydrogen atmosphere produced infiltration of the inlay casting gold into the spherical metal powder skeleton. No distortion of the skeleton occurred and the shrinkage of the block from the master process shrinkage averaged 0.79%. Rockwell "B" hardness averaged 96.

EXAMPLE 20

Two hundred g. —325 mesh (less than 44 μm) "Vertx" Co-6 cobalt-based spherical metal powder was mixed with 2.0 g of "Epon" 828 thermosetting resin for 5 minutes. One-half gram epoxy curing catalyst (Shell Oil Co., Type F-1) was added and mixed for about two minutes. Lastly, 8.0 g. of butyl stearate was added to produce a smooth putty consistency after about five minutes additional mixing. This mixture was fed into a vibrating mold preheated to 66° C., de-aired under a vacuum of 1 Torr and repressurized to ambient pressure. The article was then maintained at 66° C. for ½ hour to cure the thermosetting resin and provide rigidity to the molded article. The article was demolded, packed in an alumina bed and heated to 1010° C. in an argon atmosphere containing 5% hydrogen as in Example 1. The lightly sintered article in the shaped of a two-inch (5.08 cm) cube was coated with an aerosol suspension of zirconia and infiltrated with copper at 1110° C. for 45 minutes.

EXAMPLE 21

A die casting cavity in the shape of a serrated knob approximately ½ inch (1.27 cm) in diameter and ½ inch (1.27 cm) long was prepared using the procedure of Example 1. A male model of the serrated knob was used and generation reversal was effectuated with two-component casting material sold under the trademark "Carbalon" 122G. The individual components of the casting material were cooled to 50° F. (10° C.) and deaired for 5 minutes under roughing pump vacuum (approximately 30 Torr). Equal portions of the two components were mixed and poured over the male master which had been placed in a suitable container so as to contain the casting material. The cast material covering the male master was deaired for about one minute under roughing pump vacuum and cured for about 1 hour at 50° F. (10° C.). The male model was then demolded from the cured female replica, and the replica was allowed to cure for an additional 24 hours at room temperature. The replica die cavity so produced is a female pattern reversal of the original male model.

The female replica die cavity was replicated according to procedure of Example 1 using a "Stellite" 1 —325 mesh (less than 44 μm diameter) cobalt-base alloy and 4.61 parts of "Emerest" 2642. The green molded die cavity was lightly sintered at 1130° C. and the resulting metal skeleton was infiltrated with a copper alloy containing nickel (15%) and tin (7%). Infiltration was accomplished in a hydrogen atmosphere with a 45 minutes infiltration period and an infiltration temperature of 1110° C. Zinc, heated to a temperature of 500° C. in an air oven, was poured into the infiltrated die cavity. The zinc was allowed to solidify and the casting was removed from the cavity. No reaction appeared to occur between the zinc and the die cavity wall.

Various modifications and alterations of the invention will become apparent to those skilled in the art without departing from the scope and spirit of the invention, and it should be understood that this invention is not to be limited to the illustrative embodiments and examples set forth herein.

What is claimed is:

1. A shaped, homogeneous, monolithic, metal article comprising at least 60 percent by volume of a first continuous phase of spherical non-refractory metal particles comprising cobalt or cobalt alloy, which particles are metallurgically integral at their contiguous points of contact in the form of a skeleton with perceptible necking, when viewed by a light microscope, between the largest contiguous particles thereof, and as a minor portion a second continuous phase of metal which has a melting point of at least 25° Kelvin lower than the melting point of the lowest melting of said spherical non-refractory particles and which occupies the volume of said article not occupied by said skeleton, said article thereby comprising two intermeshed matrices and being substantially void free.

2. The metal article of claim 1 wherein said non-refractory spherical metal particles comprise a distribution of diameters in the range of about 1 to 200 μm.

3. The metal article of claim 2 wherein said non-refractory spherical metal particles are less than 45 μm in diameter.

4. The metal article of claim 3 wherein said non-refractory spherical metal particles have a calculated surface area in the range of about $1.8 \times 10^{-2}$ m$^2$/g to $14.2 \times 10^{-2}$ m$^2$/g.

5. The article of claim 1 wherein the ratio of the melting temperature of said second continuous phase to the melting temperature of said first continuous phase is less than about 0.98 when both temperatures are expressed on the Kelvin scale.

6. The metal article of claim 5 wherein said ratio is less than about 0.95.

7. The metal article of claim 5 wherein said ratio is greater than about 0.5.

8. The metal article of claim 5 wherein said ratio is greater than about 0.6.

9. The metal article of claim 1 wherein said first continuous phase has a melting temperature in the range of 1273° Kelvin to 2073° Kelvin and said second continuous phase has a melting temperature in the range of 700° Kelvin to 2048° Kelvin.

10. The article of claim 1 wherein said first continuous phase or said second continuous phase or both said first continuous phase and said second continuous phase are hardenable metals or alloys.

11. The metal article of claim 1 wherein said second continuous phase comprises metal selected from the group consisting of copper, silver, gold and alloys containing one or more of copper, silver and gold.

12. The article of claim 1 wherein said first continuous phase is an alloy containing cobalt and said second continuous phase is an alloy containing copper.

13. The article of claim 1 wherein said first continuous phase is an alloy containing cobalt and said second continuous phase is gold or an alloy containing gold.

14. A shaped, homogeneous, monolithic, metal article having a working surface, said article comprising at least 60 percent by volume and not more than 80 percent by volume, of a first continuous phase of spherical, non-refractory metal particles comprising cobalt or cobalt alloy, said particles having a distribution of diameters in the range of about 1 to 45 m, and a surface area in the range of about $1.8 \times 10^{-2}$ m$^2$/g to $14.2 \times 10^{-2}$ m$^2$/g, said particles being metallurgically integral at their contiguous points of contact in the form of a skeleton with perceptible necking, when viewed by a light microscope, between the largest contiguous particles thereof, and a second continuous phase of a metal which has a melting point of at least 25° Kelvin lower than the melting point of the lowest melting of said spherical non-refractory particles and which occupies the volume of said article not occupied by said metallurgically integral spherical particles, said article thereby comprising two intermeshed matrices and being substantially void free.

15. The metal article of claim 1 wherein said molded metal article is a dental prostheses.

16. A metal article of claim 1 wherein said non-refractory article is an injection molding die cavity.

17. The metal article of claim 1 wherein said molded article is a metal die casting cavity.

18. The metal article of claim 1 wherein said second continuous phase wets said first continuous phase.

19. A process for forming a shaped, monolithic, metal article comprising the steps of:

heating a mixture of non-refractory spherical metal powder comprising cobalt or cobalt alloy and fugitive organic binder comprising a thermoplastic material above the softening temperature of said binder;

molding the resulting plastic mass in a heated flexible mold to form an essentially void-free green molded article having the shape and size of the mold;

supporting the resulting green molded article in a non-reactive refractory powder;

heating the said green molded article to volatilize the organic binder and to lightly sinter said non-refractory spherical metal powder and thereby form a coherent monolithic metal skeleton;

cooling the resulting monolithic metal skeleton and infiltrating said monolithic metal skeleton with a second metal with a melting point that is at least 25° K. lower than the melting point of the lowest melting said spherical metal powder, to form an infiltrated molded metal article.

20. A process for forming a molded, monolithic, non-refractory metal article comprising the steps of:

mixing a non-refractory, spherical metal powder comprising cobalt or cobalt alloy with a fugitive organic binder comprising a thermoplastic material;

heating the resulting powder-binder mixture above the softening temperature of said organic binder to form a plastic mass;

feeding the plastic mass mixture into a warmed, elastic mold;

vibrating the mold and its warm contents at reduced pressure;

maintaining the mold and its warm contents without vibrating at a temperature above the softening temperature of the organic binder for 1 to 24 hours;

vibrating the mold and its contents;

cooling the mold and its contents;

demolding said contents by applying a vacuum to the outside of said elastic mold, thereby forming a green molded article;

packing the green molded article in a non-reactive refractory powder;

heating said green molded article to volatilize the organic binder and to lightly sinter the non-refractory powder, thereby forming a metallurgically integral, monolithic skeleton;

placing solid infiltrant metal contiguous to, but not touching, said skeleton such that upon melting the melted infiltrant will, under the influence of gravity, flow toward and contact the surface of said skeleton;

heating said skeleton and infiltrant metal above the melting point of said infiltrant metal, whereby said infiltrant melts and flows toward said skeleton surface and infiltrates into the skelton through the surface of said skeleton;

cooling the resulting infiltrated skeleton to form a molded, non-refractory spherical powder metal article.

21. The process in accordance with claim 20 wherein said plastic mass is cooled into a solid, the resulting solid powder-binder mixture is milled to a granular consistency, and the granular powder-binder mixture is heated above the softening temperature of said binder prior to further processing.

22. The process in accordance with claim 20 wherein said non-refractory skeleton is placed in direct contact with solid infiltrant metal.

23. A process for forming a molded, monolithic, non-refractory metal article comprising the steps of:

mixing a non-refractory, spherical metal powder with a fugitive organic binder comprising a thermoplastic material;

heating the resulting powder-binder mixture above the softening temperature of said organic binder to form a plastic mass;

feeding the plastic mass mixture into a warmed, elastic mold;

vibrating the mold and its warm contents at reduced pressure;

maintaining the mold and its warm contents without vibrating at a temperature above the softening temperature of the organic binder for 1 to 24 hours;

vibrating the mold and its contents;

cooling the mold and its contents;

demolding said contents by applying a vacuum to the outside of said elastic mold, thereby forming a green molded article;

packing the green molded article in a non-reactive refractory powder;

heating said green molded article to volatilize the organic binder and to lightly sinter the non-refractory powder, thereby forming a metallurgically integral, monolithic skeleton;

coating a portion of the surface of said metallurgically integral, monolithic skeleton with zirconia powder leaving a portion of said skeleton surface free of zirconia powder;

placing solid infiltrant metal contiguous to, but not touching said skeleton such that upon melting the melted infiltrant will, under the influence of gravity, flow toward and contact said uncoated portion of said skeleton;

heating said non-refractory skeleton and said infiltrant metal above the melting point of said infiltrant metal whereby said infiltrant flows toward said skeleton surface portion free of zirconia powder and infiltrates into the non-refractory skeleton through the said skeleton surface portion free of zirconia powder; and cooling and resulting infiltrated skeleton to form a molded, spherical powder metal article.

24. A process for forming a molded, monolithic, non-refractory metal article comprising the steps of:

mixing a non-refractory, spherical metal powder with a fugitive organic binder comprising a theremoplastic material;

heating the resulting powder-binder mixture above the softening temperature of said organic binder to form a plastic mass;

feeding the plastic mass mixture into a warmed, elastic mold;

vibrating the mold and its warm contents at reduced pressure;

maintaining the mold and its warm contents without vibrating at a temperature above the softening temperature of the organic binder for 1 to 24 hours;

vibrating the mold and its contents;

cooling the mold and its contents;

demolding said contents by applying a vacuum to the outside of said elastic mold, thereby forming a green molded article;

packing the green molded article in a non-reactive refractory powder;

heating said green molded article to volatilize the organic binder and to lightly sinter the non-refractory powder, thereby forming a metallurgically integral, monolithic skeleton;

coating a portion of the surface of said metallurgically integral, monolithic skeleton with zirconia powder leaving a portion of said skeleton surface free of zirconia powder;

placing said non-refractory skeleton in direct contact with solid infiltrant metal;

heating said non-refractory skeleton and said infiltrant metal above the melting point of said infiltrant metal whereby said infiltrant flows toward said skeleton surface portion free of zirconia powder and infiltrates into the non-refractory skeleton through the said skeleton surface portion free of zirconia powder; and cooling the resulting infiltrated skeleton to form a molded, spherical powder metal article.

25. The process of claim 20 wherein said organic binder is a mixture of a thermoplastic material and a thermosetting material.

26. The process of claim 20 wherein said organic binder comprises organic carboxy compound selected from the group consisting of mixtures of stearic acid and oleic acid, oleic acid, stearic acid, lower alkyl esters of oleic acid, lower alkyl esters of stearic acid, polyethylene glycol esters of oleic acid, polyethylene glycol esters of stearic acid, and mixtures thereof.

27. The process of claim 26 wherein said organic binder is polyethylene glycol distearate.

28. A shaped, homogeneous, monolithic, uniformly, porous metal article comprising non-refractory spherical metal particles which are metallurgically integral at their contiguous points of contact in the form of a skeleton with perceptible necking, when viewed by light microscope, between the largest contiguous particles thereof, a portion of the surface of said metal article being coated with a layer of a material that inhibits surface blooming on said metal article.

29. A metal article in accordance with claim 28 wherein said surface blooming inhibitor is zirconia powder.

* * * * *

UNITED STATES PATENT AND TRADEMARK OFFICE
CERTIFICATE OF CORRECTION

PATENT NO. : 4,431,449

DATED : February 14, 1984

INVENTOR(S) : Kenneth R. Dillon and Richard L. Terchek

It is certified that error appears in the above-identified patent and that said Letters Patent is hereby corrected as shown below:

Col. 4, line 53, "power-binder" should read -- powder-binder --.

Col. 9, line 68, "out" should read -- cut --.

Col. 10, line 57,"of" (second occurrence) should read -- at --

Col. 11, line 43, insert a comma after "physical".

Col. 16, line 32, "shaped" should read -- shape --.

Col. 18, line 4, "45 m" should read -- 45 µm --.

Col. 20, lines 8-9, "theremoplastic" should read
-- thermoplastic --.

Signed and Sealed this

Twenty-third Day of April 1985

[SEAL]

Attest:

DONALD J. QUIGG

Attesting Officer

Acting Commissioner of Patents and Trademarks